(12) United States Patent
Byers et al.

(10) Patent No.: US 10,123,754 B2
(45) Date of Patent: Nov. 13, 2018

(54) WRAPPABLE STERILE RADIATION SHIELD DRAPE, COMBINATION OF A RADIATION SHIELD AND STERILE DRAPE THEREFOR AND METHOD OF PROVIDING A STERILE DRAPE ABOUT A RADIATION SHIELD

(71) Applicant: TIDI CFI Products, LLC, Fenton, MI (US)

(72) Inventors: Terry Byers, Flushing, MI (US); Michael W. Czop, Fenton, MI (US); Samba Toure, Grand Blanc, MI (US); Richard A. Weaver, Linden, MI (US)

(73) Assignee: TIDI Products, LLC, Neenah, WI (US)

( * ) Notice: Subject to any disclaimer, the term of this patent is extended or adjusted under 35 U.S.C. 154(b) by 435 days.

(21) Appl. No.: 14/565,228

(22) Filed: Dec. 9, 2014

(65) Prior Publication Data
US 2015/0090273 A1 Apr. 2, 2015

Related U.S. Application Data

(63) Continuation of application No. 13/355,741, filed on Jan. 23, 2012, now Pat. No. 8,925,553.
(Continued)

(51) Int. Cl.
*A61B 46/00* (2016.01)
*G21F 3/03* (2006.01)
(Continued)

(52) U.S. Cl.
CPC .............. *A61B 6/107* (2013.01); *A61B 46/00* (2016.02); *G21F 3/03* (2013.01); *A61B 2090/0481* (2016.02)

(58) Field of Classification Search
CPC ......... A61B 46/00; A61B 46/23; A61B 46/27; A61B 46/20; A61B 2046/201;
(Continued)

(56) References Cited

U.S. PATENT DOCUMENTS 3,729,747 A * 5/1973 Belkin ............... A41D 13/1209
2/114
3,777,749 A 12/1973 Collins
(Continued)

FOREIGN PATENT DOCUMENTS

EP 1321947 6/2003

*Primary Examiner* — Kari Rodriquez
*Assistant Examiner* — Camtu Nguyen
(74) *Attorney, Agent, or Firm* — Boyle Fredrickson, S.C.

(57) ABSTRACT

A wrappable sterile radiation shield drape, a wrappable sterile radiation shield drape in combination with a radiation shield, and a method of providing a sterile surface about a suspended radiation shield is provided. The drape includes a flexible wall having a sterilized outer surface. The wall has opposite side edges extending between upper and lower ends and an upper fastener adjacent its upper end. The upper fastener is configured to releasably fix the upper end of the wall relative to the radiation shield. The wall further includes an edge fastener adjacent at least one of its side edges. The edge fastener is configured to releasably maintain the wall in a wrapped configuration about the radiation shield. The wall further includes at least one flap attached adjacent the upper end, wherein the flap includes a pocket configured to receive a shoulder extension portion of the radiation shield.

6 Claims, 5 Drawing Sheets

Related U.S. Application Data

(60) Provisional application No. 61/434,875, filed on Jan. 21, 2011.

(51) Int. Cl.
*A61B 6/10* (2006.01)
*A61B 90/00* (2016.01)

(58) Field of Classification Search
CPC ............ A61B 6/107; A61B 2090/0436; A61B 2090/0481; G21F 3/00; G21F 3/02; G21F 3/025; G21F 3/03; G11F 3/035
USPC ......... 128/849, 851–852, 854, 856; 378/204, 378/208
See application file for complete search history.

(56) References Cited

U.S. PATENT DOCUMENTS

| | | | | |
|---|---|---|---|---|
| 4,523,335 A | * | 6/1985 | Scrivens | A41D 13/1209 2/114 |
| 5,015,864 A | * | 5/1991 | Maleki | G21F 3/02 250/515.1 |
| 5,015,865 A | * | 5/1991 | Sayers | G21F 3/03 250/515.1 |
| 5,115,140 A | * | 5/1992 | Rodriguez | G21F 3/02 174/388 |
| 7,343,919 B2 | | 3/2008 | Czajka et al. | |
| 7,543,587 B2 | | 6/2009 | Yardan et al. | |
| 7,549,179 B1 | | 6/2009 | Saied | |
| 8,188,453 B2 | | 5/2012 | Kirschenbaum | |
| 8,716,687 B2 | | 5/2014 | Goldstein et al. | |
| 2008/0078962 A1 | * | 4/2008 | Hoxha | A61B 6/107 250/516.1 |
| 2009/0184269 A1 | * | 7/2009 | Rees | G21F 3/02 250/516.1 |
| 2010/0107320 A1 | * | 5/2010 | Rees | A61B 6/107 2/456 |
| 2012/0167896 A1 | | 7/2012 | Stang | |
| 2012/0280004 A1 | * | 11/2012 | Huang | A47G 25/90 223/85 |

* cited by examiner

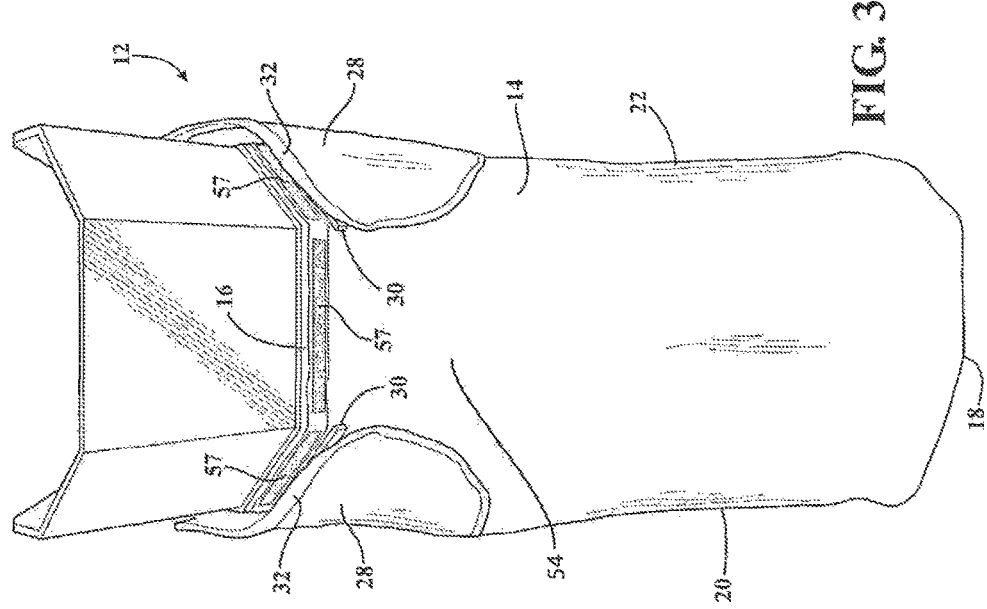
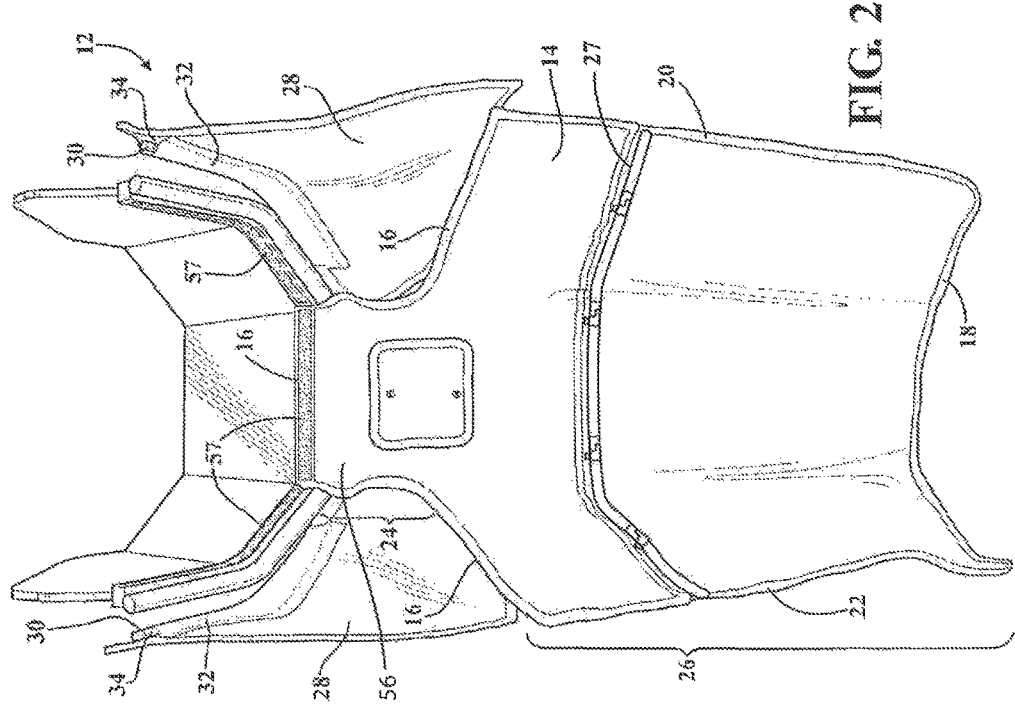

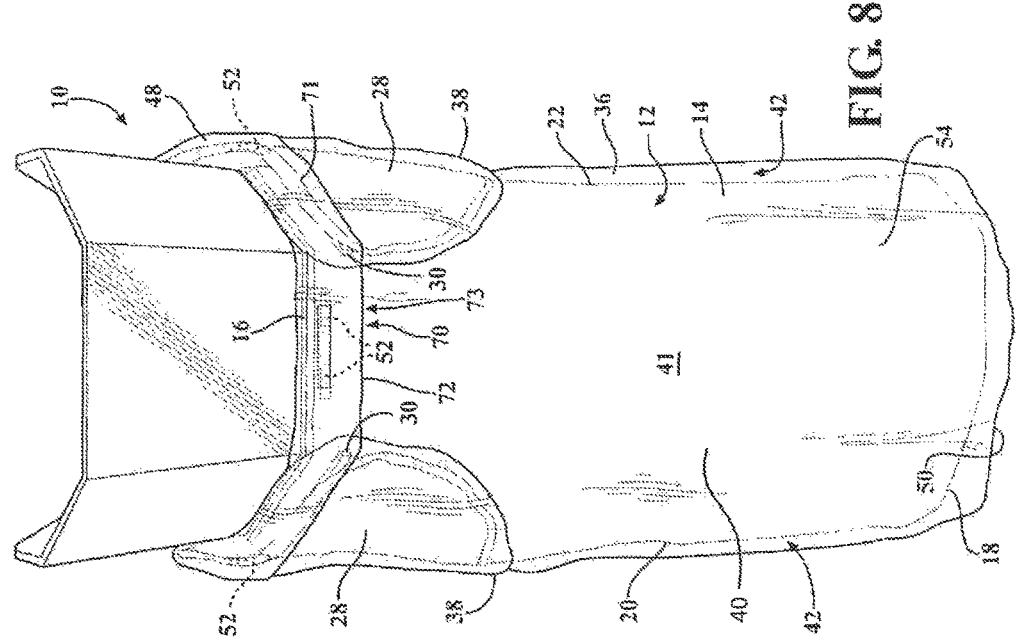
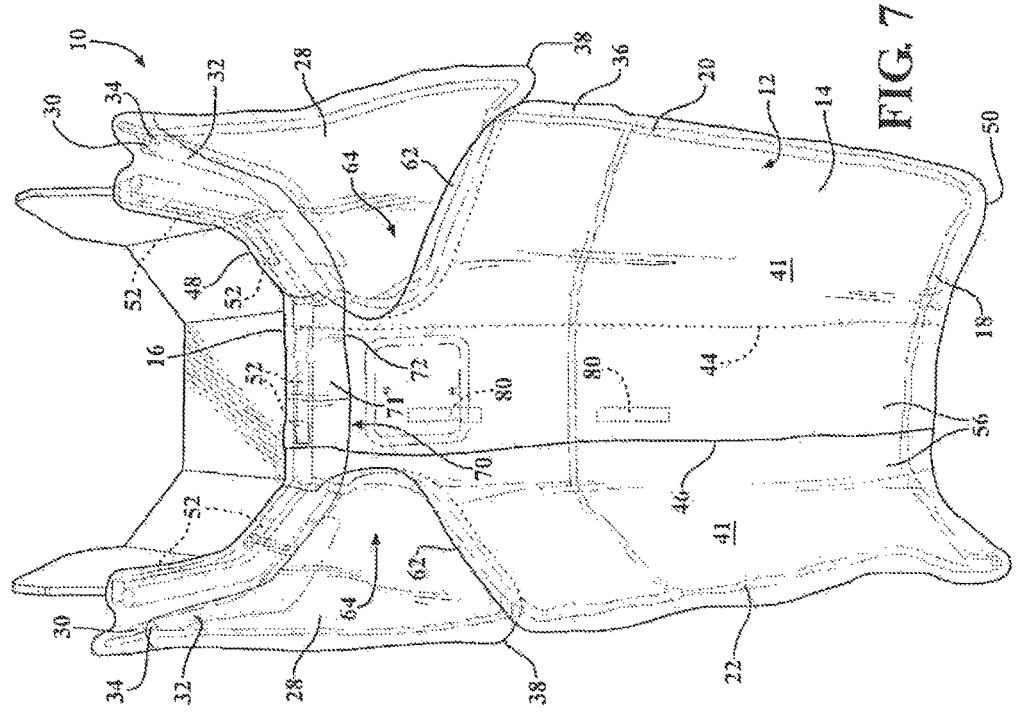

WRAPPABLE STERILE RADIATION SHIELD DRAPE, COMBINATION OF A RADIATION SHIELD AND STERILE DRAPE THEREFOR AND METHOD OF PROVIDING A STERILE DRAPE ABOUT A RADIATION SHIELD

CROSS-REFERENCE TO RELATED APPLICATION

This application is a continuation application of U.S. patent application Ser. No. 13/355,741, filed Jan. 23, 2012, now Pat. No. 8,925,553 which issued on Jan. 6, 2015, which claimed the benefit of U.S. Provisional Application Serial No. 61/434,875, filed Jan. 21, 2011, both of which are incorporated herein by reference in their entirety.

BACKGROUND OF THE INVENTION

1. Technical Field

This invention relates generally to sterilized drapes used in medical procedures, and more particularly to sterilized drapes configured to enclose radiation shields in medical procedures and to their method of installation.

2. Related Art

It is common to apply sterilized drapes to medical equipment used in medical procedures to prevent having to sterilize the equipment itself. The drapes present an external sterile surface about non-sterile surface to facilitate avoiding the contamination of the surgical theatre, thereby reducing the risk of infection to the patient. Though desirable to apply sterilized drapes to various types of medical equipment, it can prove challenging to apply the drapes about the equipment due to the various configurations thereof. Additionally, due to the complicated configurations of some sterile drapes, it can prove challenging to avoid compromising the sterile external surface of the drapes while disposing the drapes about the non-sterile surface. In addition, it can prove challenging to allow full and substantially unfettered use of the medical equipment upon applying the drapes to the equipment as a result of the drapes impeding movement of the equipment.

SUMMARY OF THE INVENTION

A wrappable sterile radiation shield drape configured to be disposed about a radiation shield while the radiation shield is hanging from a support at its top end and extending to a free bottom end is provided. The wrappable sterile radiation shield drape includes a flexible wall having a sterilized outer surface. The wall has opposite free side edges extending between an upper end and a lower end. The wall further includes at least one upper fastener adjacent its upper end, wherein the at least one upper fastener is configured to releasably fix the upper end of the wall relative to the radiation shield. The wall further includes at least one edge fastener adjacent at least one of its opposite free side edges. The at least one edge fastener is configured for releasable attachment adjacent the other of the opposite free side edges to releasably maintain the wall in a wrapped configuration about the radiation shield. The wall further includes at least one flap attached to the wall adjacent the upper end of the wall, wherein the flap includes a pocket configured to receive a shoulder extension portion of the radiation shield.

In accordance with another aspect of the invention, the drape has a pair of flaps providing a pair of pockets configured to receive a pair of shoulder extension portions of the radiation shield.

In accordance with another aspect of the invention, a wrappable sterile radiation shield drape in combination with a radiation shield is provided. The radiation shield is configured to substantially conform with and shield a user's body from exposure to radiation. The radiation shield has a top end configured to hang from a support and an opposite bottom end with opposite sides extending between the top and bottom ends, and further includes at least one shoulder extension portion adjacent the top end. The radiation shield drape includes a flexible wall having a sterilized outer surface. The wall has opposite free side edges extending between an upper end and a lower end. The wall has at least one upper fastener adjacent its upper end, wherein the at least one upper fastener is configured to releasably fix the upper end of the wall relative to the radiation shield. The wall has at least one edge fastener adjacent at least one of its opposite free side edges, wherein the at least one edge fastener is configured for releasable attachment adjacent the other of the opposite free side edges to releasably maintain the free side edges in attached relation with one another and the wall in wrapped relation about the radiation shield. The wall further includes at least one flap attached to the wall adjacent the upper end of the wall, wherein the flap includes a pocket configured to receive a corresponding shoulder extension portion of the radiation shield.

In accordance with another aspect of the invention, a method of providing a sterile surface about a suspended radiation shield having at least one shoulder extension portion is provided. The method includes suspending a radiation shield configured to substantially contour to a user's body from a support. Further, providing a flexible wall having a sterilized outer surface with opposite free side edges extending between a lower end and an upper end with at least one upper fastener adjacent the upper end and at least one edge fastener adjacent at least one of the opposite free edges, and having at least one flap including a pocket. Then, fixing the flexible wall relative to the radiation shield by operably attaching the upper fastener operably to the radiation shield without compromising the sterility of the outer surface. Further, wrapping the opposite free side edges of the flexible wall about the radiation shield and fixing the opposite free side edges with one another via the edge fastener. Further yet, inserting the at least one shoulder extension portion of the radiation shield into the pocket of a corresponding flap on the wall.

BRIEF DESCRIPTION OF THE DRAWINGS

These and other aspects, features and advantages of the invention will become more readily appreciated when considered in connection with the following detailed description of presently preferred embodiments and best mode, appended claims and accompanying drawings, in which:

FIG. 2 is a rear view of the radiation shield;

FIG. 3 is a front view of the radiation shield;

FIG. 7 is a rear view of the radiation shield shown with the drape wrapped thereabout; and FIG. 8 is a front view of FIG. 7.

DETAILED DESCRIPTION OF PRESENTLY PREFERRED EMBODIMENTS

Figure 1:
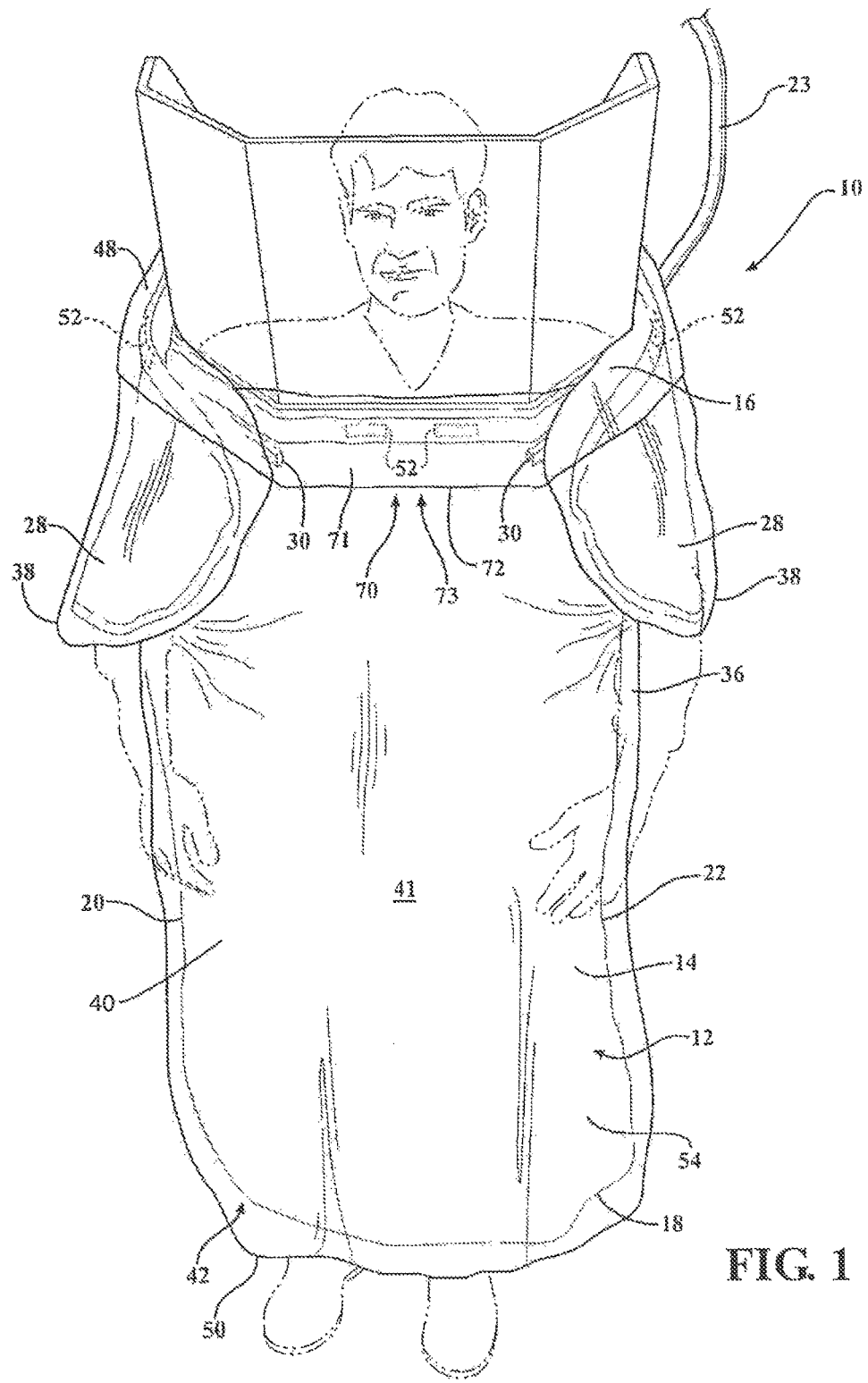
FIG. 1 is a front view of a sterilized drape constructed in accordance with one aspect of the invention wrapped about a radiation shield configured to substantially conform with a user.

Referring in more detail to the drawings, FIG. 1 illustrates a front view of a flexible sterile radiation shield drape, referred to hereafter as drape 10, constructed in accordance with one aspect of the invention wrapped and releasably fixed about a radiopaque radiation shield, referred to hereafter as shield 12. The drape 10 is configured to be wrapped about the shield 12 using a circumferential wrapping installation process that allows the drape 10 to conform or substantially conform to the shield 12 without compromising the sterility of the outer sterile drape surfaces. As such, with the drape 10 being conformed or substantially conformed to the shape of the shield 12, a user is able to retain maximum degrees of movement without interference from the drape 10. Further, the sterile flexible drape 10 allows the shield 12 to maintain its full range of unimpeded movement as though the drape 10 were not present. In addition, the drape 10 is provided as a one-piece assembly, thereby keeping the number of components having to be handled to provide a sterile outer surface barrier about the shield 12 to a minimum. With the drape 10 providing sterility to the shield 12, the need to repeatedly sterilize the shield 12 between uses is negated.

As best shown in FIGS. 2 and 3, the shield 12 has a main body, identified generally at 14, with opposite top and bottom ends, also referred to as upper and lower ends 16, 18, respectively, with laterally spaced sides 20, 22 extending between the ends 16, 18. The body 14 can be supported by a suspending mechanism, also referred to as support 23, such as with the suspending mechanism being operably attached to the upper end 16 of the shield 12, such that the shield 12 hangs freely from the support 23 to its free lower end 18, for example. It should be recognized that the support 23 can be suspended from an overhead ceiling, such as via a trolley system, or from a floor supported structure, each being capable of allowing the shield 12 to move 3-dimensionally along X, Y and Z axes, as desired. Further, the body 14 can be constructed of any suitable material capable of acting as a radiopaque barrier to radiation, such as lead or a leaded material, for example, and can have an internal frame structure, such as disclosed in U.S. patent application Ser. No. 12/099,077 filed on Apr. 7, 2008, which is incorporated herein by reference in its entirety. The internal frame structure of the shield 12 is provided as horizontally extending (generally parallel to a floor surface) foldable members that can be readily folded by the user, as desired, to wrap the sides 20, 22 of the shield 12 circumferentially toward one another to enclose or substantially enclose the sides of the user's body with the shield 12, thereby providing a radiopaque barrier to radiation about the sides of the user. The foldable members can be configured to remain in their folded configuration via friction at the respective pivot joints of the foldable members, and thus, upon being folded or pivoted, the foldable members tend to remain in their desired folded orientation until acted on by a suitable external force to intentionally move the foldable members to or toward their unfolded, extended position. Accordingly, the foldable members can be folded inwardly toward one another and outwardly away from one another, as desired by the user, to allow the shield 12 to be selectively wrapped and configured about the user and unwrapped from the user.

As best shown in FIG. 2, the shield 12 has an upper reduced width region 24 extending upwardly from a lower increased width region 26. The upper reduced width region 24 is intended to extend along the user's chest or sternum toward the neck region of the user to allow full and unfettered movement of the user's arms, such as may be necessary during a surgical procedure. The lower increased width region 26 of the shield 12 has a generally uniform rectangular shape, by way of example, bounded by the sides 20, 22, the lower end 18 and laterally spaced outer portions of the upper end 16. The lower increased width region 26 has the aforementioned foldable members 27 extending generally from one side 20 to the other side 22 to allow the lower region 26 to be folded or wrapped circumferentially into a generally C-shaped configuration at least partially about the user's body, as discussed.

The shield 12 can further include at least one, and shown here as a pair of laterally spaced radiopaque shoulder shield portions or covers, also referred to as shoulder extension portions 28. The shoulder extension portions 28, by way of example and without limitation, are shown here as being detached from the main body 14 and supported in a hanging fashion from a support frame member 30 of the aforementioned suspending mechanism. When in place, the shoulder extensions 28 shield the user's shoulder region against radiation, while at the same time allowing the user to retain full flexibility and mobility in that the shoulder extension portions 28 are able to move freely with the movement of the user's shoulders and arms. Accordingly, the user's arms can extend between the body 14 and the shoulder extension portions 28, as desired, to allow the user to retain full mobility during a surgical procedure. The shoulder extension portions 28 are represented, by way of example and without limitation, as being generally triangular in shape, with one edge or side 32 of each extension 28, shown as an uppermost edge, having a receptacle or elongate pocket 34 (FIGS. 1-3) for receipt of the supporting frame member 30.

The drape 10, as best illustrated in FIGS. 1 and 6-8, includes a main body, identified generally at 36, configured to wrap about and contain the body 14 of the shield 12 and providing a corresponding number of flaps, shown here as a pair of laterally spaced flaps 38, configured to receive the shoulder extension portions 28 of the shield 12 therein. The flaps 38 are provided to accommodate the number of shoulder extensions 28 on the shield 12, and thus, it should be recognized that the drape 10 could be constructed having one or no flaps, if desired. Further, to facilitate handling, among other things, the flaps 38 are attached to the main body 36, such as by a suitable adhesive, tape, fastener (e.g. hook and loop), or weld joint, identified generally at 39, for example, and thus, the drape 10 can be handled as a single piece of material.

The main body 36 has a planar, or generally planar, flexible wall 40 with a sterilized outer surface 41 and a sterilized inner surface 43 that circumferentially encloses a cavity 42 sized for receipt of the shield body 14 therein. The outer surface 41 is sterilized to maintain sterility within the surgical theater while in use, and the inner surface 43 is sterilized as a result of the main body 36 being sterilized. It should be recognized that the inner surface 43 eventually becomes unsterile upon being disposed about and engaging the unsterile shield 12. The wall 40 is constructed generally as a flat single layer sheet of flexible, preferably impervious material, having laterally spaced free side edges 44, 46, respectively, that extend between upper and lower ends 48, 50.

To facilitate disposing the drape 10 about the shield 12 such that the drape 10 is fixed relative to the shield 12, the upper end 48 has at least one, and shown as a plurality of end fasteners 52, such as one portion of the hook and loop-type fastener, for example, attached adjacent the upper end 48. As shown, by way of example and without limitation, four such fasteners 52 are attached along an inner portion of a front face 54, for example, and six such fasteners 52 are attached along an inner portion of a rear face 56, for example. As best shown in FIGS. 2 and 3, it should be recognized that a corresponding number of fasteners; a single elongate fastener, or a plurality of fasteners 57, configured for releasable attachment to the fasteners 52, are provided adjacent the upper end 16 of the shield 12. The fasteners 57 are provided for releasable attachment to the fasteners 52, and thus, can be provided as the other portion of the hook and loop-type fastener, for example, wherein the fastener(s) 57 can be provided directly on the shield 12 and/or on the frame member 30 supporting the shield 12.

Figure 5:
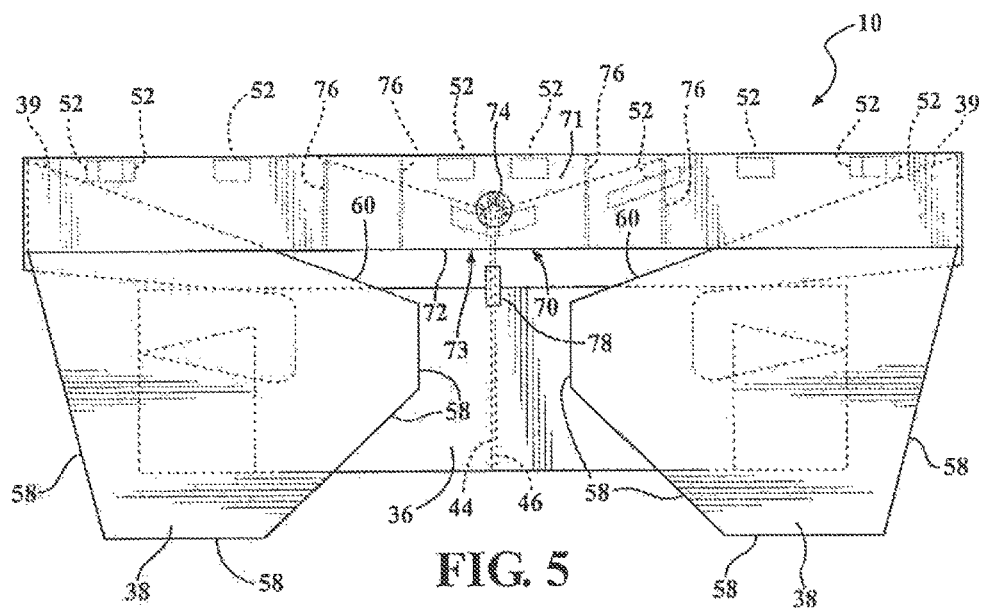
Figure 6:
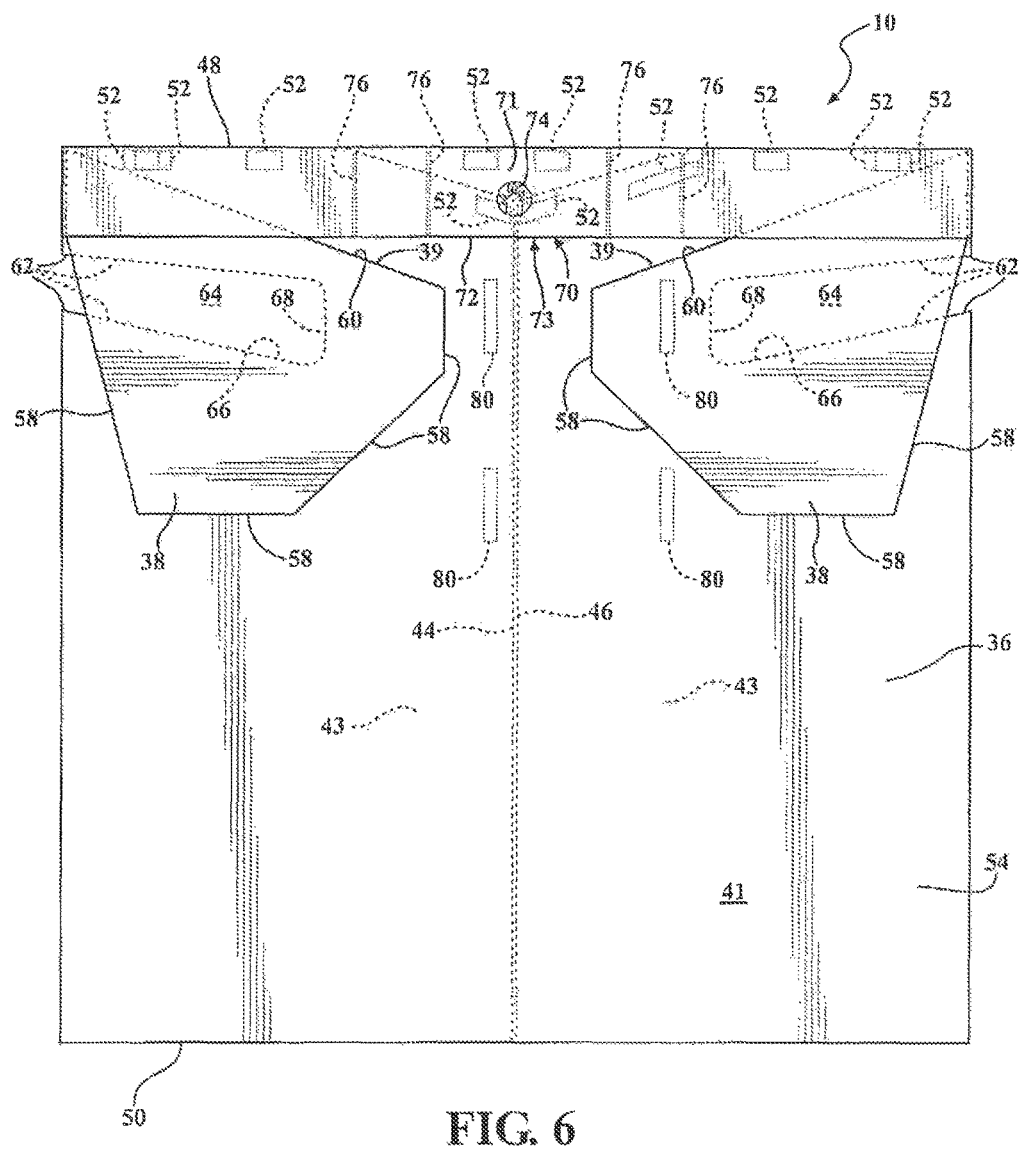

The flaps 38 are constructed having a shape that conforms with or substantially conforms with the shape of the shoulder extension portions 28. As best shown in FIGS. 5 and 6, the flaps 38 are generally bag-shaped having a closed end 58 and closed sides 58 and an open end 60. The open end 60 provides an opening sized to receive the shoulder extension portions 28 therein.

To facilitate providing conformity of the drape 10 to the shield 12, as best shown in FIG. 6, the body 36 of the drape 10 has a pair of laterally extending recesses 62 configured to follow the contour of the upper end 16 of the shield 12 and to provide windows or spaces 64 through which the user's arms can freely extend without having to move and otherwise manipulate material of the drape 10. Accordingly, while wrapping the drape 10 about the shield 12, the increased width region 26 of the shield upper end 16 is received in a pocket formed by a lower edge 66 the recesses 62, while a generally vertical edge 68 of each recess 62 also conforms in a close fit about the reduced width region 24 of the shield 12.

Figure 4:
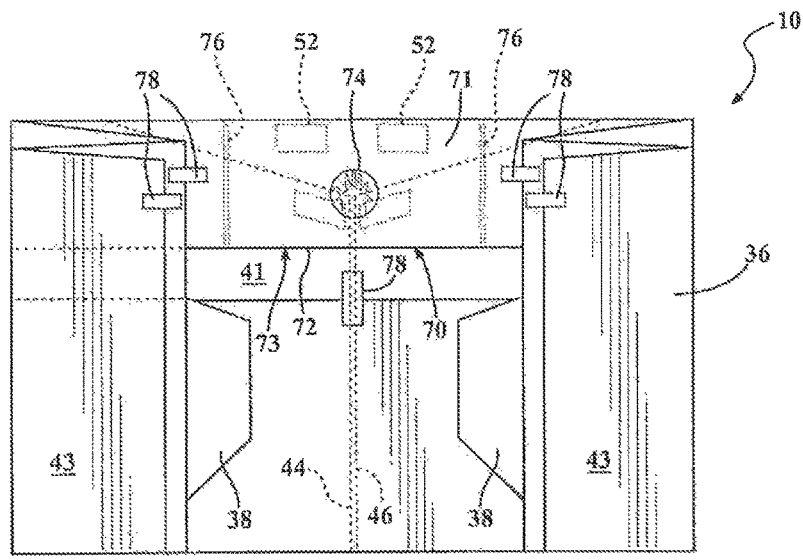
FIGS. 4-6 show progressive stages of the sterilized drape being unfolded from an as packaged, folded state.

In accordance with another aspect of the invention, a method of providing a sterile drape about a suspended radiation shield is provided. The method, with reference to the features discussed and identified above with reference numerals, includes removing the sterilized drape 10 from a sterile package and partially unfolding the drape 10, as shown generally in FIG. 4. Upon bringing the drape 10 into the configuration shown in FIG. 4, the user places their hand(s) in a pocket 70 located generally centrally between the opposite side edges 44, 46. The pocket 70 is provided by an everted flap or portion 71 that extends to a free edge 72 of the wall 40, thereby forming the pocket 70 with a closed upper edge and an opening 73 facing toward the lower end 50. The everted portion 71 and pocket 70 is shown as extending circumferentially about the upper end 48, wherein the location intended for insertion of the user's hand is clearly identified by a hand symbol 74, for example. Further, the user places the generally centrally located fasteners 52 adjacent the hand symbol 74 into fastening engagement with the corresponding centrally located fastener or centrally located portion of the fastener 57 on the shield 12. The upper end 48 is maintained in its everted configuration via a fastening mechanism, such as at least one bond joint provided via an adhesive or weld joint, and shown as a plurality of bond joints identified generally at 76. Then, upon fixing the upper end 48 of the drape 10 relative to the shield 12, the user can further unfold the drape 10 by tearing or otherwise separating fasteners 78 that temporarily maintain the drape 10 in both a horizontally and vertically folded configuration, which facilitate maintaining the lower end 50 of the drape 10 within the sterile surgical field while wrapping the drape 10 about the shield 12. Then, upon tearing the fasteners 78, the drape 10 can assume its fully unfolded configuration, as shown partially unfolded in FIG. 5 and fully unfolded in FIG. 6. Then, the free side edges 44, 46 can be wrapped circumferentially about the shield 12 while manipulating the sides 20, 22 of the shield 12 into the pockets formed by the bonded lower edges 66 of the recesses 62. Further, as shown in FIG. 7, the free side edges 44, 46 of the drape 10 are wrapped into overlapping relation with one another to bring at least one side fastener, and shown as a plurality of side fasteners 80 adjacent the free side edges 44, 46 into mating fastening engagement with one another, such as those having mating fastener components, e.g. hook and loop type or snap type components, and to bring a pair of the fasteners 52 adjacent the upper end 48 into releasably fastened engagement with one another. It should be recognized that a single side fastener and/or upper fastener could be used, such as an adhesive temporarily covered by release paper, thereby negating the need to have fasteners with mating components, such as hook and loop or snap type fasteners. Further yet, while wrapping the drape 10, the shoulder extension portions 28 of the shield 12 are disposed in the corresponding flaps 38 of the drape 10. Accordingly, the entire shield 12 is circumferentially wrapped and enclosed by the sterile drape 10, wherein the sterile outer surface 41 of the drape maintains sterility within the surgical field. Then, upon completing the surgical procedure, the drape 10 can be readily disposed and the shield 12, without having to be sterilized, can be covered again for a new procedure via a new drape 10.

Obviously, many modifications and variations of the present invention are possible in light of the above teachings. It is, therefore, to be understood that within the scope of the appended claims, the invention may be practiced otherwise than as specifically described.

What is claimed is:

1. A radiation shield drape system comprising,
 a radiation shield comprising:
   foldable members that can be folded, said foldable members being configured to substantially conform with a body of a user;
   a top end configured to hang from a support;
   an opposite bottom end with opposite sides extending between said top and bottom ends; and
   at least one shoulder extension portion configured to move freely with movement of a shoulder and an arm of said user; and
 a wrappable sterile radiation shield drape comprising:
   a flexible wall having a sterilized outer surface, said flexible wall having opposite free side edges extending between an upper end and a lower end;
   at least one upper fastener adjacent said upper end, said at least one upper fastener being configured to releasably fix said upper end of said flexible wall relative to said radiation shield;
   at least one edge fastener adjacent at least one of said opposite free side edges, said at least one edge fastener being configured for releasable attachment adjacent said other of said opposite free side edges to releasably maintain said opposite free side edges in attached relation with one another and said flexible wall in wrapped relation about said radiation shield when said foldable members are folded around said body of said user; and
   at least one flap attached to said flexible wall adjacent said upper end of said flexible wall, said at least one flap having a closed end, a first closed side, a second closed side, and a open end to form a generally bag-shape configured to receive said at least one shoulder extension portion of said radiation shield;
 a pair of laterally extending recesses on either side of said flexible wall, said pair of laterally extending recesses configured to provide spaces through which said arm of said user can extend wherein said radiation shield is configured to substantially conform with and shield a user's body from exposure to radiation;

wherein said at least one shoulder extension portion is contained within said generally bag-shaped during movement of said shoulder and an arm of said user; and wherein said wrappable sterile radiation shield drape conforms to said radiation shield without compromising sterility of said flexible wall.

2. The combination of claim 1 wherein a pair of said flaps is attached adjacent said upper end, each one of said pair of flaps being configured to receive a separate shoulder extension portion of said radiation shield.

3. The combination of claim 2 wherein said pair of flaps are attached to said flexible wall via weld joints.

4. The combination of claim 1 wherein said at least one edge fastener is provided as a fastener having coupling fastener components positioned adjacent each of said opposite free edges.

5. The combination of claim 1 wherein said at least one upper fastener is provided as a fastener component configured for releasable attachment to another fastener component on said radiation shield.

6. The combination of claim 1 wherein said at least one upper fastener is a fastener component configured for releasable attachment to another fastener component on said radiation shield, said radiation shield has a pair of shoulder extension portions; and said flexible wall has a pair of flaps, each of said pair of flaps having a generally bag-shape;

wherein said pair of shoulder extension portions fit within said generally bag-shape of said pair of flaps.

* * * * *